United States Patent [19]

Willis et al.

[11] Patent Number: 5,663,997

[45] Date of Patent: Sep. 2, 1997

[54] GLASS COMPOSITION DETERMINATION METHOD AND APPARATUS

[75] Inventors: James E. Willis; Andrew L. Heilveil, both of Austin, Tex.; Robert Dejaiffe, Dunkirk, N.Y.

[73] Assignees: Asoma Instruments, Inc., Austin, Tex.; Dunkirk International Glass and Ceramics Corporation, Dunkirk, N.Y.

[21] Appl. No.: 379,696

[22] Filed: Jan. 27, 1995

[51] Int. Cl.⁶ .................................................. G01N 23/223
[52] U.S. Cl. .......................... 378/45; 378/44; 378/48
[58] Field of Search ............................ 378/45, 44, 48

[56] References Cited

U.S. PATENT DOCUMENTS

| | | | |
|---|---|---|---|
| 3,351,198 | 11/1967 | Wyman | 209/111.6 |
| 3,435,950 | 4/1969 | Suverkrop | 209/73 |
| 3,650,396 | 3/1972 | Gillespie et al. | 209/3 |
| 3,802,558 | 4/1974 | Rhys | 209/75 |
| 3,919,548 | 11/1975 | Porter | 378/45 |
| 3,970,254 | 7/1976 | Marsh | 241/1 |
| 3,980,180 | 9/1976 | Jamieson | 209/111.6 |
| 4,057,146 | 11/1977 | Castaneda et al. | 209/75 |
| 4,271,966 | 6/1981 | Crowley | 250/431 X |
| 4,373,638 | 2/1983 | Schapper | 209/570 |
| 4,513,868 | 4/1985 | Culling et al. | 209/581 |
| 4,585,343 | 4/1986 | Schave et al. | 356/237 |
| 4,699,273 | 10/1987 | Suggi-Liverani et al. | 209/580 |
| 4,781,742 | 11/1988 | Hill et al. | 65/29 |
| 4,848,590 | 7/1989 | Kelly | 209/564 |
| 5,081,658 | 1/1992 | Imai et al. | 378/45 |
| 5,125,943 | 6/1992 | Cole | 65/27 |
| 5,148,923 | 9/1992 | Fraenkel et al. | 209/539 |
| 5,206,699 | 4/1993 | Stewart et al. | 250/458.1 |
| 5,256,886 | 10/1993 | Wolf et al. | 250/574 |
| 5,260,576 | 11/1993 | Sommer, Jr. et al. | 378/54 X |
| 5,314,071 | 5/1994 | Christian et al. | 209/4 |
| 5,335,791 | 8/1994 | Eason | 209/588 |
| 5,350,118 | 9/1994 | Mitchell et al. | 239/551 |
| 5,424,959 | 6/1995 | Reyes et al. | 378/45 X |

FOREIGN PATENT DOCUMENTS 1162173  8/1969  United Kingdom ............ 378/45

OTHER PUBLICATIONS

ELKE Ceramic Removal System, MSS, Inc. No date.

*Primary Examiner*—David P. Porta
*Attorney, Agent, or Firm*—Arnold, White & Durkee

[57] ABSTRACT

A method and apparatus for determining the composition of glass, and for sorting glass according to composition. Glass of unknown composition is irradiated and an x-ray fluorescence spectrum is detected from the glass. The detected x-ray fluorescence spectrum is then compared with a plurality of fluorescence spectra corresponding to glasses of known composition. The glass of unknown composition is then determined to correspond in composition to the glass of known composition having an x-ray fluorescence spectrum most closely matching the spectrum detected from the glass of unknown composition. The glass may then be sorted according to determined composition. In operation, a substantially continuous stream of glass pieces is irradiated and detected while the stream is moving. Once the composition of a piece of glass in the stream is determined, it is diverted into an appropriate container of like compositioned glass.

16 Claims, 15 Drawing Sheets

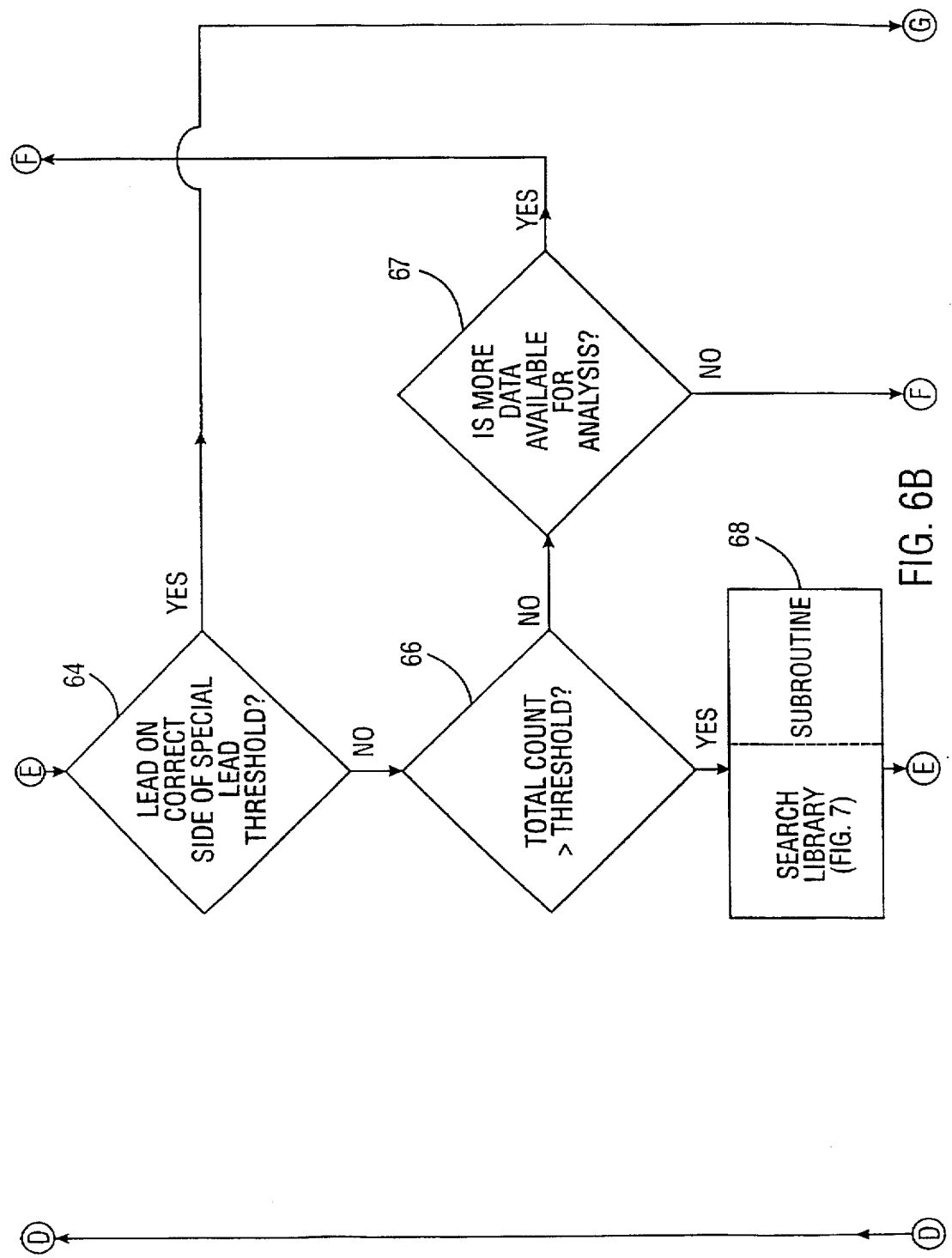

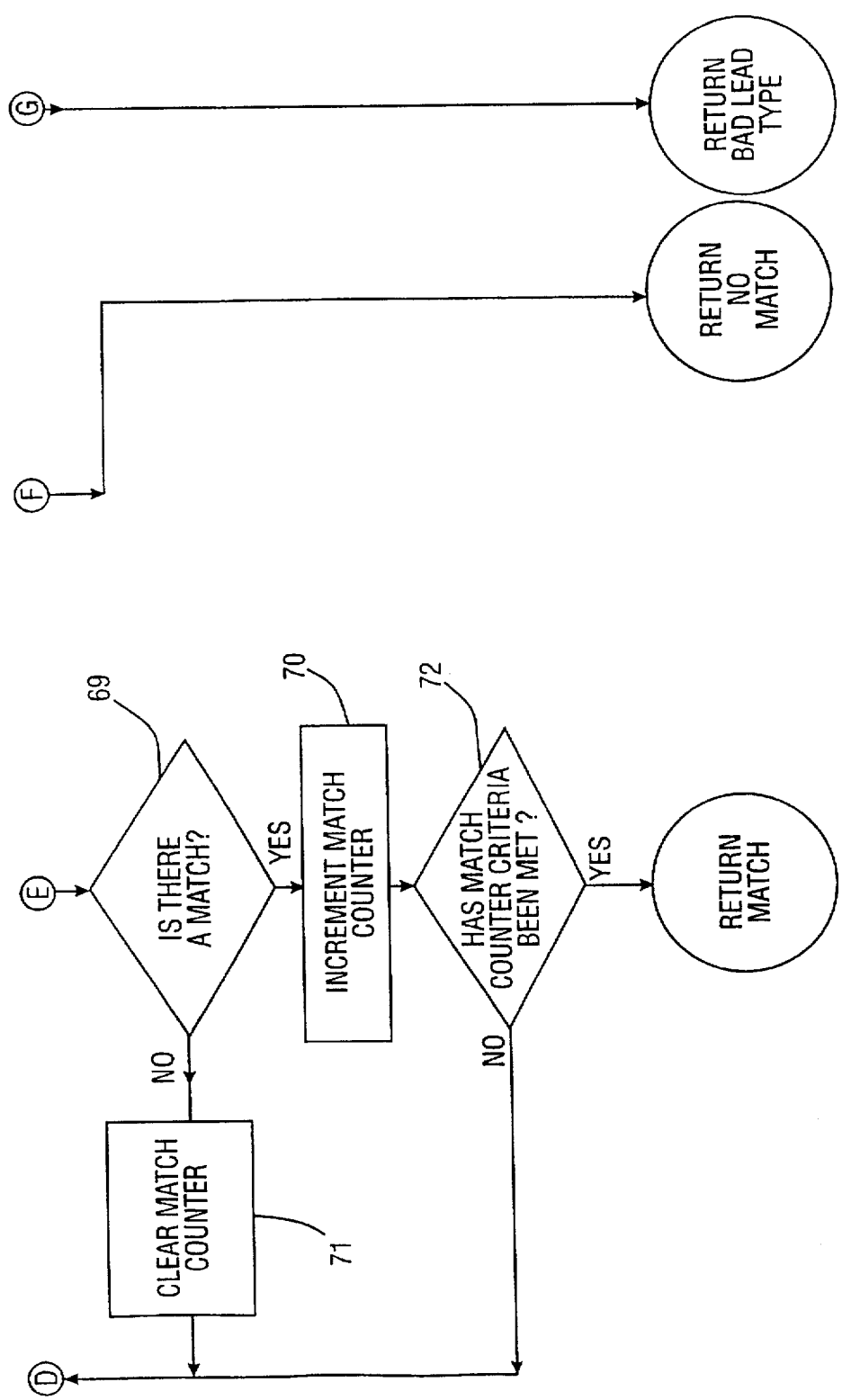

GLASS COMPOSITION DETERMINATION METHOD AND APPARATUS

BACKGROUND OF THE INVENTION

The invention relates to a method and apparatus for determining the composition of glass of unknown composition, and for sorting glass according to composition.

The environmental regulations of the U.S. and other nations currently classify the glass and other components of television tubes and color computer monitors as hazardous waste. Due to this classification, the direct landfilling of tubes which are found to be defective or which are broken in manufacturing, is no longer permitted. The disposal of this material requires a stabilization treatment before it can be legally landfilled. Elsewhere in the world there are more stringent restrictions on the disposal of these materials.

To further complicate the disposal issue, discussions have been started at various regulatory agencies concerning the disposal of cathode ray tubes (CRTs) from television sets and color computer monitors at the end of their useful life. There are approximately 250,000,000 television sets and 60,000,000 computer monitors in use in the United States. The disposal of 5% of the television sets and 10% of the computer monitors would represent an estimated 130,000 tons of CRT glass annually. Landfill disposal is the least desirable option for both the generator and the municipal planners.

The environmental issue which is of most concern relative to the disposal of the CRT glass is the potential for lead to be released from the materials. The most vulnerable portion of the CRT tube is the frit which is used to join the face plate (panel) to the funnel. This frit is comprised largely of lead oxide, which is slightly soluble in weak acids and thus vulnerable to leaching and migration into ground waters when buried in a landfill.

The CRT glass contains substantial quantities of lead oxide (PbO). Generally, lead oxide in this form is inert and environmentally stable. If the lead bearing glass is broken up or ground up into a fine powder and exposed to an acidic environment, such as might exist in a landfill, small quantities of lead can be leached out.

In addition, the interior coatings of older television CRTs contain high levels of cadmium compounds which are toxic. The landfilling of these CRTs can lead to the leaching of the cadmium compounds and their release into the ground water. The current manufacturing processes utilize different coatings which are not known to be toxic or carcinogenic; however, toxicological studies are being performed on a continuous bases to insure the safety of those who come in contact with the materials.

A perception exists that large amounts of lead would potentially be disposed of by the landfilling of electronic assemblies. It is therefore desirable to avoid landfilling these materials in order to lower costs, reduce the environmental risk and to assure the public safety.

The avoidance of landfill disposal should preferably encompass the total use of the glassy materials of the television CRTs, defective tubes and debris from manufacturing. Much of the current practice involves the reformulation of these glasses into raw materials. The raw materials are then used to make new products including electrical resistance glass; decorative glass; glass for the absorption of low-level radiation from low-level radioactive wastes; glass for retroreflective use and high density glass. In these cases, the products are unique in their function or in their substitution for other glasses. In all cases, the products have greater value in us or are lower priced substitutes forexisting products manufactured from non-recycled glass. A competitive advantage exists in the use of waste streams as raw materials for the manufacture of these unique products.

While the reformulation of CRT derived cullet into some new products does not require careful control of cullet formulation, if the glasses could be successfully separated by formulation from waste stream, then they would be more easily reformulated into useful products. By identifying the glass composition, it would be easier to channel cullet to the appropriate process for inclusion as a raw material in the production of a final salable product.

In addition to the utilization of the separated glasses as raw materials in the manufacture of secondary products, a new market has been established for the resale of the identified glass back to the CRT manufacturers for remelting. The criteria for this type of separation and recycling are very stringent and the separation requires highly accurate identification of the glass composition. CRT glass is a high quality optical glass. In order to manufacture this glass to the required quality standards, it is necessary to insure that the composition remain stable. The use of clean cullet is desirable because it allows the generator to avoid the cost of landfilling and reduces the melting costs. The remelting of cullet requires significantly less energy than melting raw materials to form the same glass. Compositional upsets can occur if the cullet is misidentified. This situation can result in large monetary losses on the order of $300/ton plus the cost of any processing.

The key component to the successful use of the discarded glass is accurate and reliable sorting. If the sorting is done accurately, the glass plant can save as much as $170/ton for materials and processing. In addition, in order to be commercially viable, sorting should be fast.

It would therefore be desirable to provide a means for accurately, reliably and quickly sorting CRT derived glass cullet according to glass composition.

SUMMARY OF THE INVENTION

The present invention satisfies the above-noted requirements by providing a method and apparatus for determining the composition of glass of unknown composition using x-ray fluorescence spectroscopy, and for sorting glass according to composition.

More particularly, the present invention uses x-ray fluorescence spectroscopy for identification of the key constituents of glass cullet. This process involves the exposure of a piece of glass to an x-ray source. The interaction of the x-rays with the elements of the glass results in a fluorescence emission spectrum of radiation which is characteristic of each o element present in the cullet. The intensities of the fluorescence emission spectrum peaks are dependent on the quantity of the elements present. By measuring the intensities of the emission fluorescence peaks, a quantitative determination of the elements present may be made.

The invention also includes a conveyor system for the presentation of the glass cullet to the x-ray system. The design results in the accurate placement of the glass thus enabling the x-ray fluorescence spectra to be acquired while permitting the efficient movement of the glass through the process.

Another feature of the invention is the utilization of x-ray fluorescence analysis as an input to a mechanical sorting system. The mechanical sorting system operates to separate the glass cullet by composition. The integration of the analysis results with the mechanical sort may be completed using various computers, programmable logic controllers and software. These devices provide the appropriate signals to the mechanical sorting devices.

BRIEF DESCRIPTION OF THE DRAWINGS

FIGS. 6A–6C are a flow chart of the sample processing method of the present invention.

DETAILED DESCRIPTION

Figure 1:
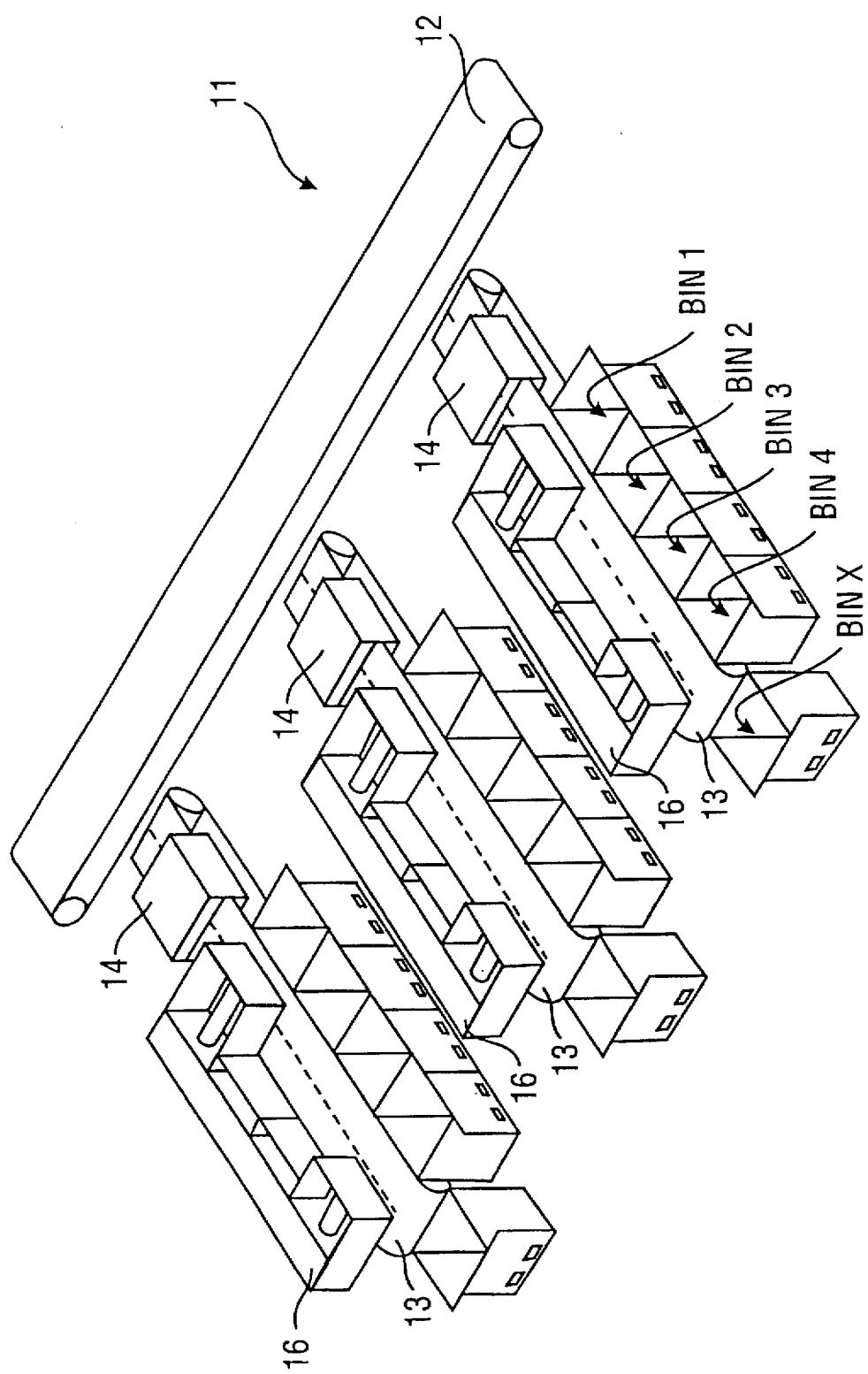
FIG. 1 is an isometric view of an exemplary apparatus in accordance with the present invention.

Referring to FIG. 1, presented in an exemplary glass sorting apparatus 11, in accordance with the present invention. In the illustrated embodiment, apparatus 11 includes three, substantially identical, glass sorting stations, each fed by common input conveyor 12. Each station includes sortation conveyor 13, which conveys glass from input conveyor 12, x-ray instrument 14, ram or pusher assemblies 16, and a number of cullet receiving bins (bin 1, bin 2, bin 3, bin 4 and bin x). As explained below in more in detail, in operation, glass cullet is conveyed along input conveyor 12, and on to a sortation conveyor 13. Conveyor 13 then conveys the cullet through x-ray instrument 14, which, in accordance with the present invention, determines the composition of the cullet using x-ray fluorescence spectroscopy. Then, as the identified cullet continues to be conveyed along sortation conveyor 13, an appropriate ram is activated to push the cullet into an appropriate bin, or if no ram is activated, to permit the cullet to fall into bin x at the end of sortation conveyor 13.

It should be noted that although three glass sorting stations are illustrated in FIG. 1, one or more stations may be used without departing from the scope of the invention. In addition, although each station illustrated in FIG. 1 is fitted with five bins, it will be understood that any number of bins may be used.

Figure 2A:
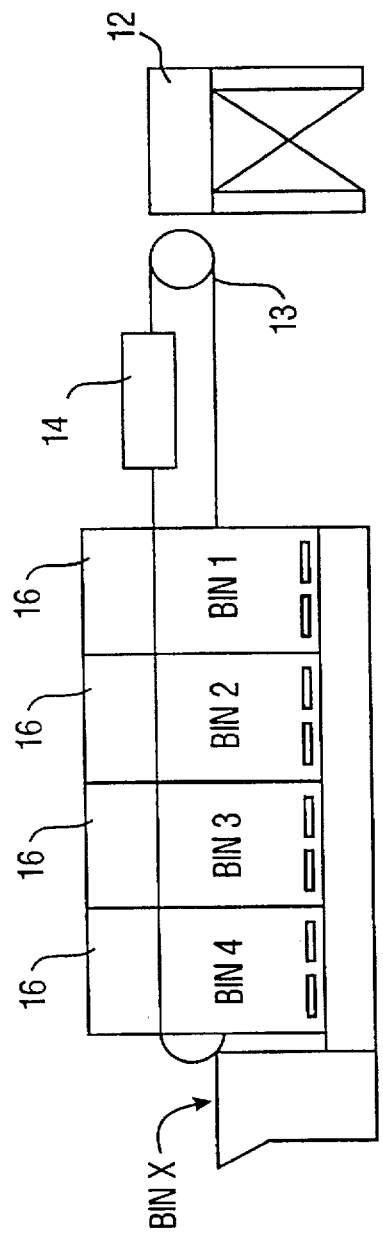
FIGS. 2A and 2B are more detailed illustrations of a portion of glass sorting apparatus of FIG. 1.
Figure 2B:
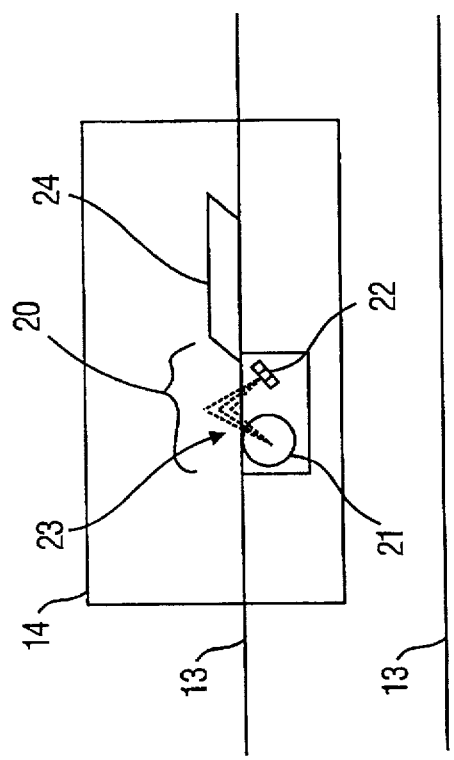

Referring now to FIGS. 2A and 2B, presented in more detail is one of the glass sorting stations illustrated in FIG. 1. A piece of glass 24, of unknown composition, is moved by sortation conveyor 13 and passes over an x-ray fluorescence spectroscopy head 20 including x-ray source 21 and x-ray detector 22. In an exemplary embodiment of the present invention, x-ray source 21 is a 60 keV, 30 milliCurie, americium ($^{241}$Am) radiation source available from Amersham, Corp., and x-ray detector 22 is a two atmosphere argon detector, model No. 45129, available from LND, Inc.; however, other radiation sources and detectors may also be used. As glass 24 moves over the x-ray fluorescence spectroscopy head 20, x-rays 23 emitted from x-ray source 21 are directed to glass 24, and detector 22 detects both x-rays that are scattered from glass 24, as well as x-ray fluorescence emitted by glass 24. X-ray source 21 preferably is fitted with a collimator (not shown).

As glass 24 moves over the x-ray fluorescence spectroscopy head 20, the x-ray signal produced by detector 22 increases, and as glass 24 moves away from head 20, the x-ray signal produced by detector 22 decreases, thus permitting the detection of the presence or absence of glass over head 20, based upon the x-ray spectrum alone, without requiring additional detecting devices.

As explained below in more detail, the x-ray spectrum produced by detector 22 is characteristic of the various constituent components present in glass 24.

In accordance with one embodiment of the present invention, measurements are taken by detector 22 approximately 16 times per second in order to be able to detect edges of glass 24. On average, in accordance with the exemplary embodiment, glass 24 spends approximately one second over x-ray head 20. Other sampling and dwell times would also be acceptable.

Figure 3:
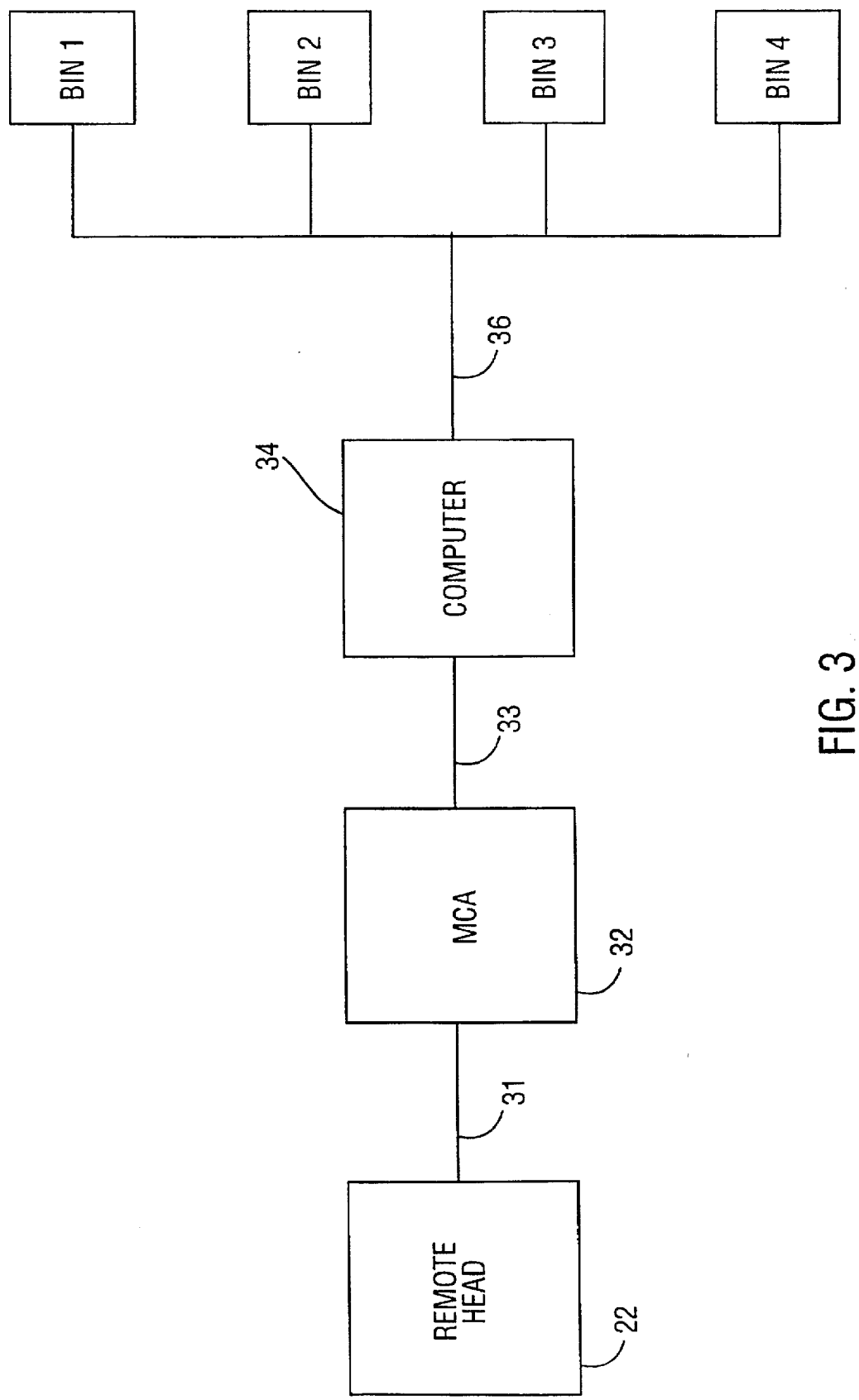
FIG. 3 is a block diagram of the glass sorting apparatus of FIG. 3.

Referring now to FIG. 3, presented is a block diagram of the signal processing components of the invention. The output of x-ray detector 22 is an analog signal appearing on line 31, which is applied to multi-channel analyzer (MCA) 32, which produces on line 33, digitized x-ray spectra (illustrated, for example, in FIGS. 9–11), for presentation to computer 34. An exemplary multi-channel analyzer usable for this purpose is commercially available from Asoma Instruments, of Austin, Tex.

Computer 34 analyzes the x-ray spectra applied on line 33 to determine the composition of the glass represented by the applied spectra. Then, computer 34 sends a signal to one of rams 16 (see also FIGS. 1, 2A and 2B) at the appropriate time to push the piece of glass that was analyzed into the appropriate bin. More than one piece of glass may be on the output conveyor simultaneously. Computer 34 schedules the activation of rams 16 to coincide with the eventual presence of the analyzed glass near the desired bin.

Figure 4:
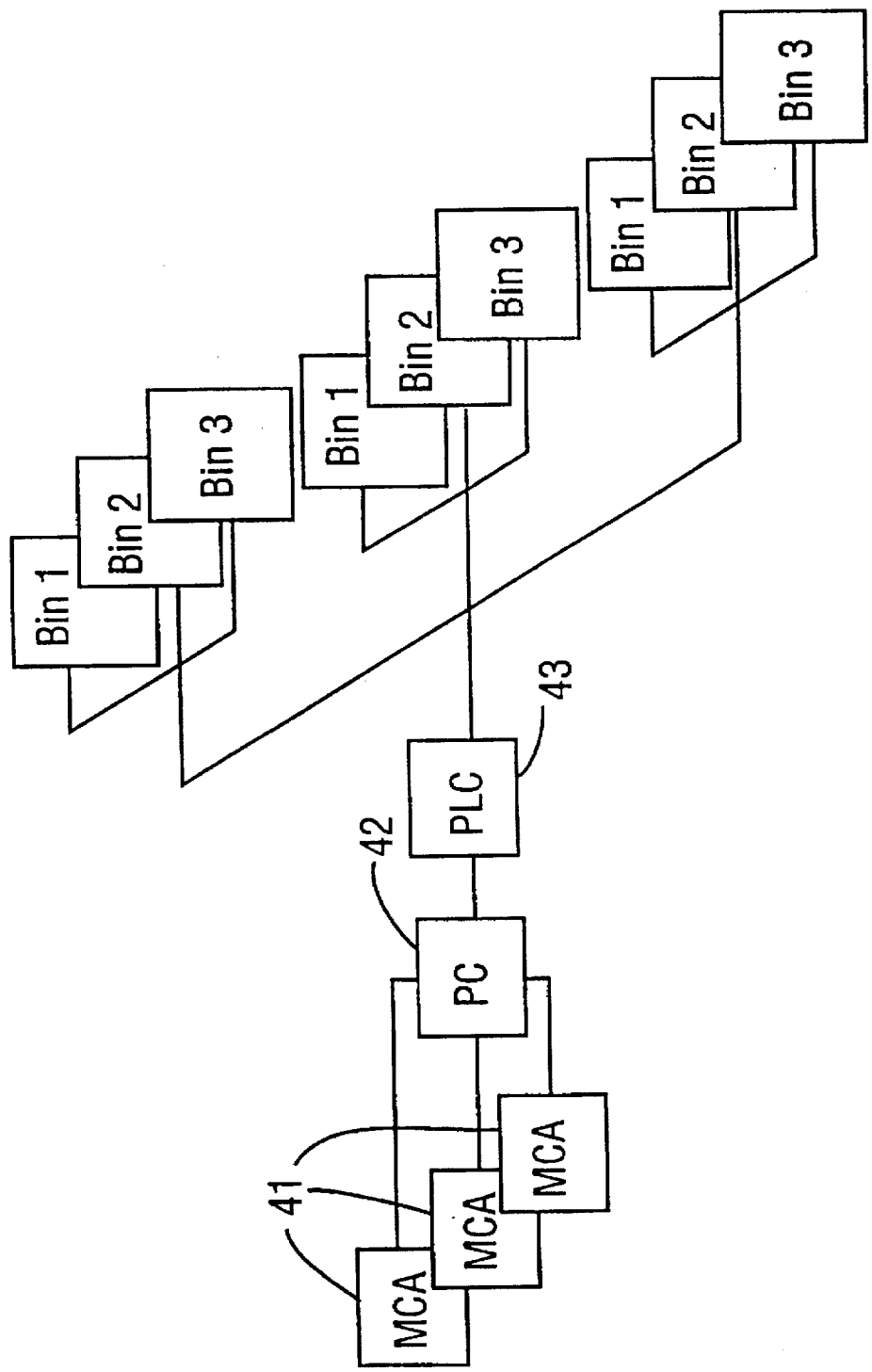
FIG. 4 is a block diagram of another embodiment of the glass sorting apparatus in accordance with the present invention.

FIG. 4 presents in block diagram form an alternate embodiment of the present invention, which includes three stations, each having a dedicated multi-channel analyzer 41, which are connected to a single computer 42. Computer 42, in turn, is connected to programmable logic controller 43 (for example, available from Allen Bradley), which in turn controls the rams 16 of all stations of the apparatus to push the sorted glass pieces into the appropriate bins after glass composition has been determined.

Referring now to FIGS. 5–7C, presented in flow chart form is the glass sorting method of the present invention. In practice, the method illustrated in the flow charts of FIGS. 5–7C is encoded in appropriate form and loaded into computer 34 or 42, in order to cause the apparatus illustrated in FIGS. 1–4 to perform the method of the present invention.

Figure 5:
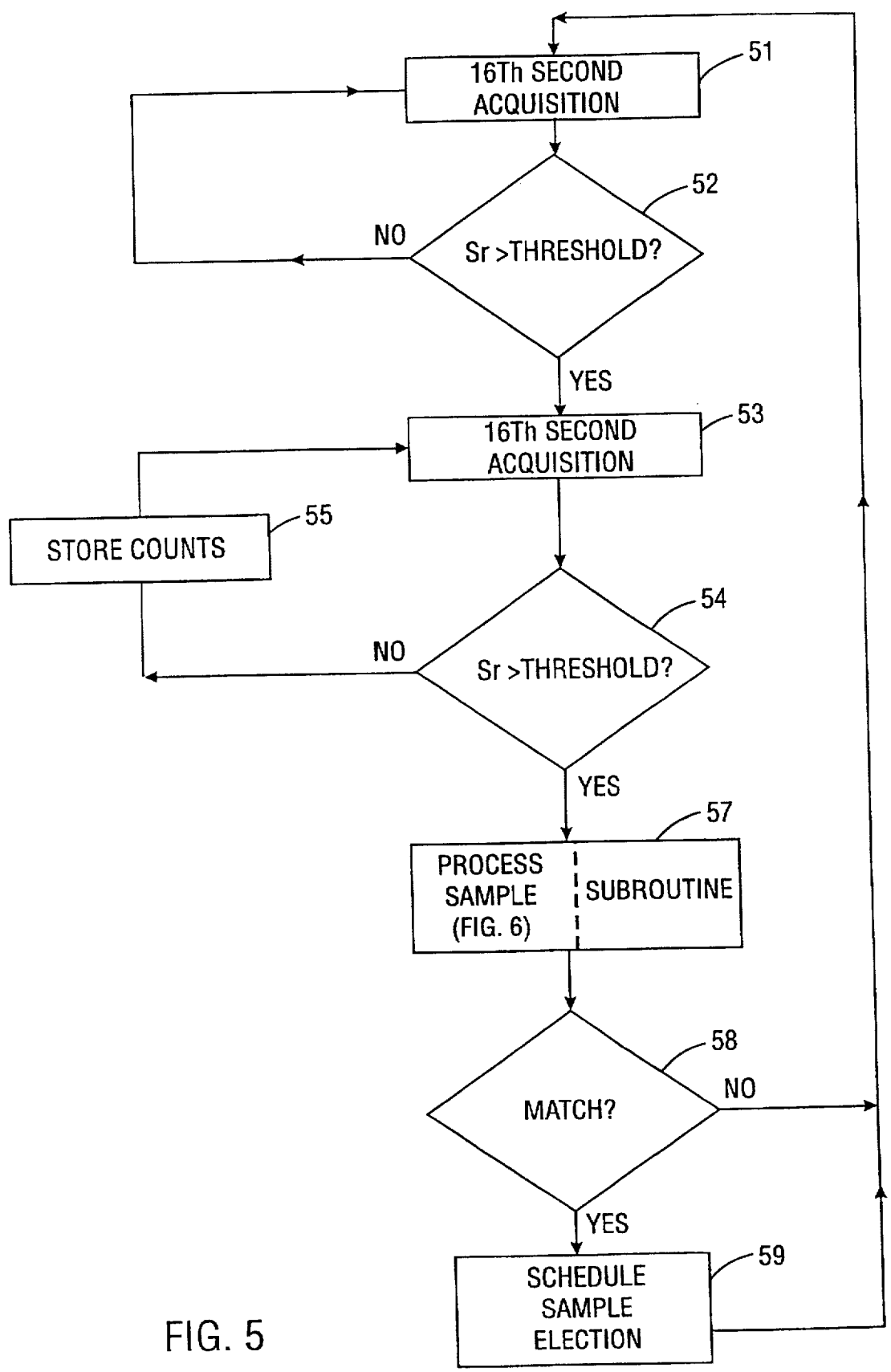
FIG. 5 is a flow chart of the glass sorting method of the present invention.

Referring to FIG. 5, operation block 51 and decision block 52 are configured in a loop to cause detector 22 (see also FIGS. 2A and 2B), to detect x-ray fluorescence and scattered x-rays. If decision block 52 detects that the x-ray intensity is greater than a predetermined threshold, it is concluded that a piece of glass is present over head 20, and control passes to block 53. Operation block 53 and decision block 54 are also configured in a loop to cause detector 22 to detect x-ray fluorescence and x-rays scattered from glass 24, while glass 24 is over head 20. During the loop, the samples are stored by block 56. If it is determined that the detected x-ray intensity has fallen below a predetermined threshold (indicating that glass 24 is leaving head 20), control passes to block 57 where the samples collected in block 56 are analyzed. This analysis is presented below in more detail with reference to FIGS. 6A–6C.

Control then passes to block 58 where it is determined whether the analysis performed in block 57 has resulted in the accurate identification of the composition of glass 24. If so, control passes to block 59, wherein a particular bin for the glass is determined and the corresponding ram is scheduled to be activated at the appropriate time to eject the glass 24 into the appropriate bin. After the scheduling of what to do with the glass is done by block 59, control turns to block 51 where the next piece of glass of unknown composition is analyzed.

The scheduling of future ramming is important to system throughput. Block 57, 58 and 59 should execute in less time than it takes conveyor 13 to present the next piece of glass, at least on the average.

The present invention thus presents a reliable, accurate, continuously operating glass sorting method and apparatus, which permits precision, automated glass sortation according to composition, resulting in commercially viable glass sortation.

Figure 6A:
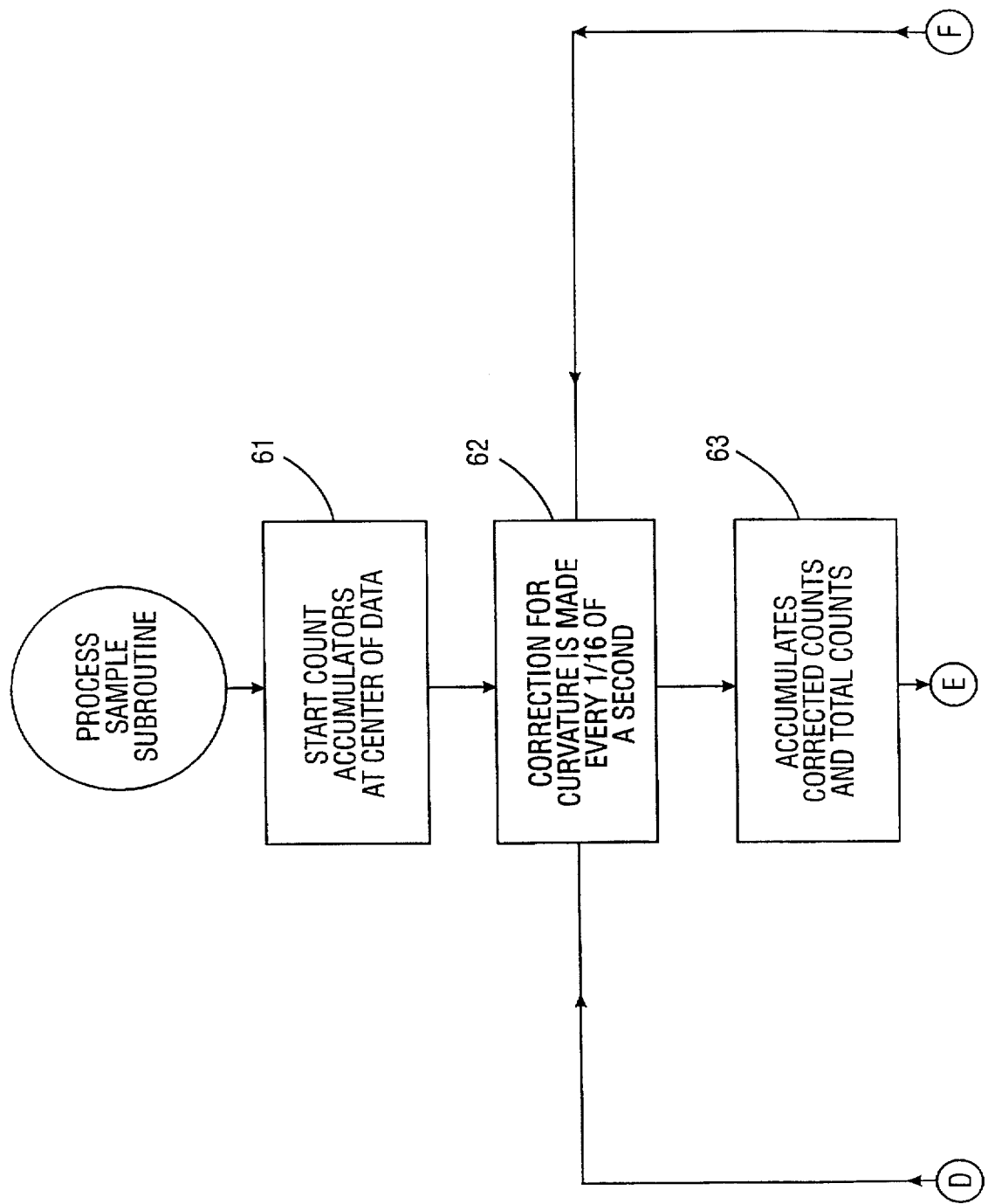

Referring now to FIGS. 6A–6C, presented in more detail is the sample processing method of step 57 of FIG. 5. Beginning in step 61, analysis has begun at the center of the data stored in block 56 (FIG. 5), ensuring that analysis has begun using data corresponding to the center of glass 24. Control then passes to block 62 where the data is corrected for the curvature of the glass. This is accomplished through a normalization procedure that produces normalized spectrum by dividing individual raw intensities, by the sum of the raw intensities at selected energies. Normalization of the raw x-ray intensity is necessary in order to correct for sample curvature and possible other sample presentation errors such as height above x-ray head and for the variable time each sample actually spent. In the present invention each of the raw x-ray intensities are divided by their sum. The resultant normalized values then sum to one.

For example, if the counts for Pb, Sr, Zr and Ba are 100, 200, 300 and 400, respectively, then the normalized counts are: 100/(100+200+300+400), 200/(100+200+300+400), 300/(100+200+300+400) and 400/(100+200+300+400), respectively. These ratios are: 0.1, 0.2, 0.3 and 0.4, respectively.

After normalization, control passes to block 63 where the corrected counts and total counts are accumulated. Then, in decision block 64, it is determined whether the portion of the spectrum corresponding to lead content of the glass indicates that the lead content of the glass is on the correct side of a predetermined threshold. "Correct side" means that if leaded glasses are to be sorted out, then the measured lead must be above the threshold; if unleaded glasses are to be sorted out, than it must be lower. This is done as a separate step as this determination can be reliable even if the match cannot be. This allows an otherwise identified glass to be sorted into leaded and unleaded "waste." The importance of this is that lead is a serious containment for unleaded glass processes. Some amount of unclassified unleaded glass may be mixed in with properly identified leaded glass with little consequence to further processing; however, if leaded glass mixes in with properly identified unleaded glass, a whole batch can be spoiled.

If glass 24 is concluded to include lead, control is returned to block 58 of FIG. 5, with an indication that the glass sample includes lead. If, on the other hand, decision block 64 determines that lead is not present in the glass sample, control passes to decision block 66 where the total number of counts is assessed. If the total number of counts is less than a predetermined number, thus indicating that the glass sample is too small for accurate composition determination, control passes to decision block 67 where it is determined whether additional data is available for analysis. If not, control is returned to decision block 58 of FIG. 5 indicating that no match for the glass under consideration can be determined. If, on the other hand, decision block 67 determines that additional data is available for analysis, control is returned to block 62.

Figure 7A:
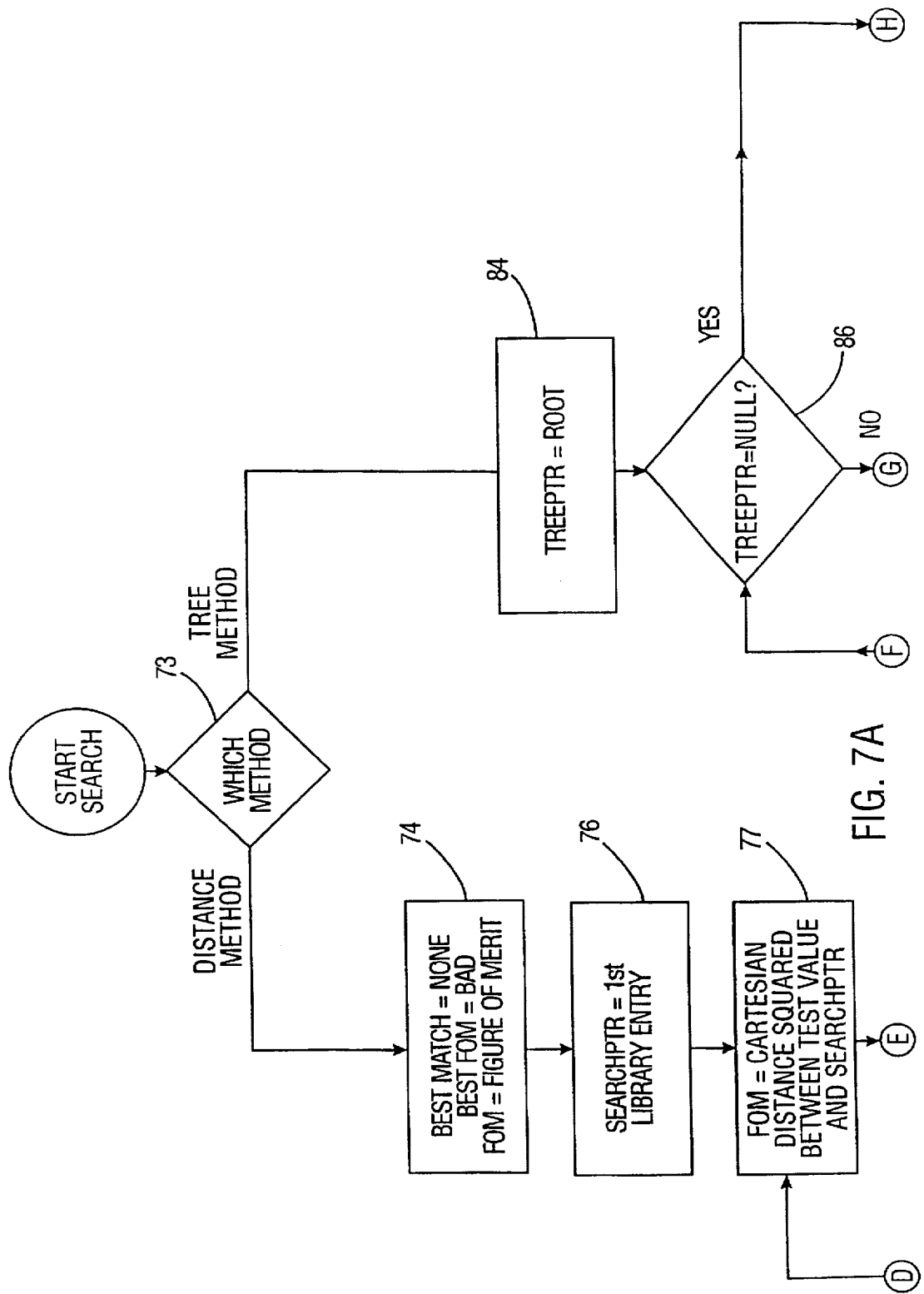
FIGS. 7A–7C are an exemplary flow chart of library searching methods, in accordance with the present invention.
Figure 7B:
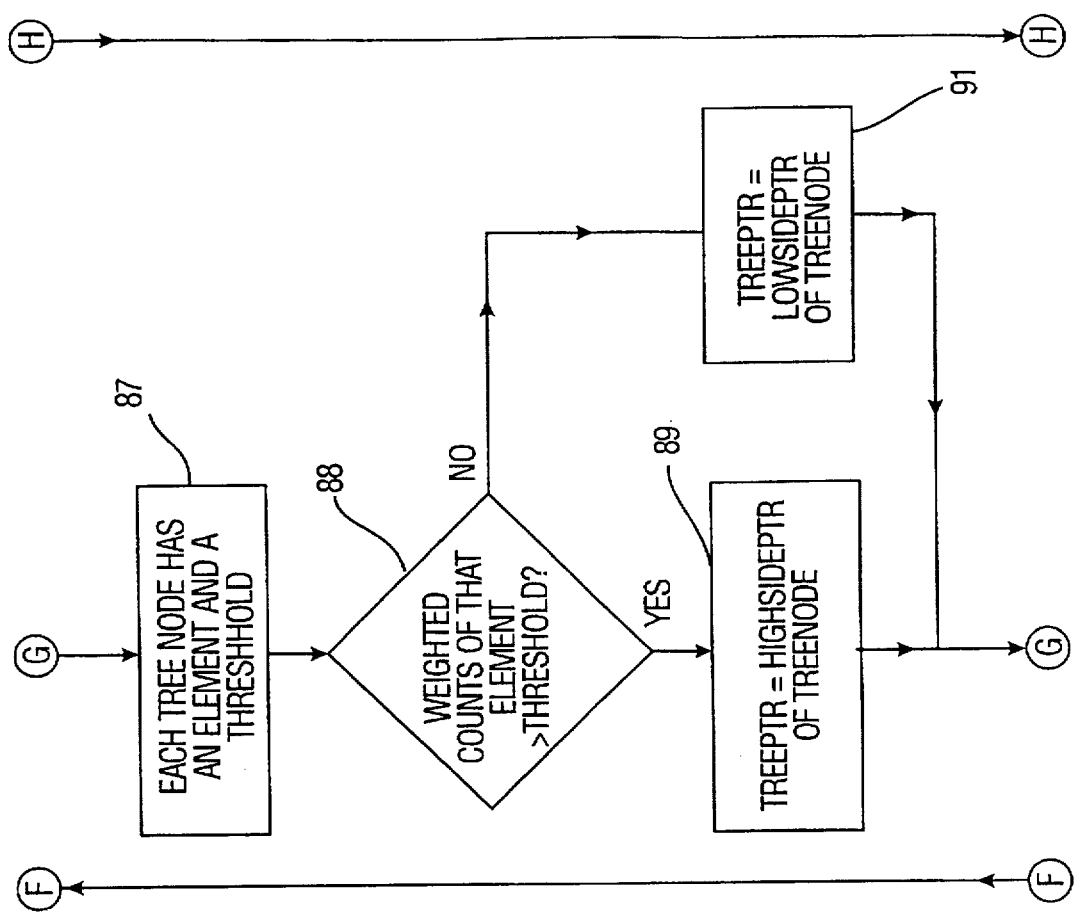
Figure 7B:
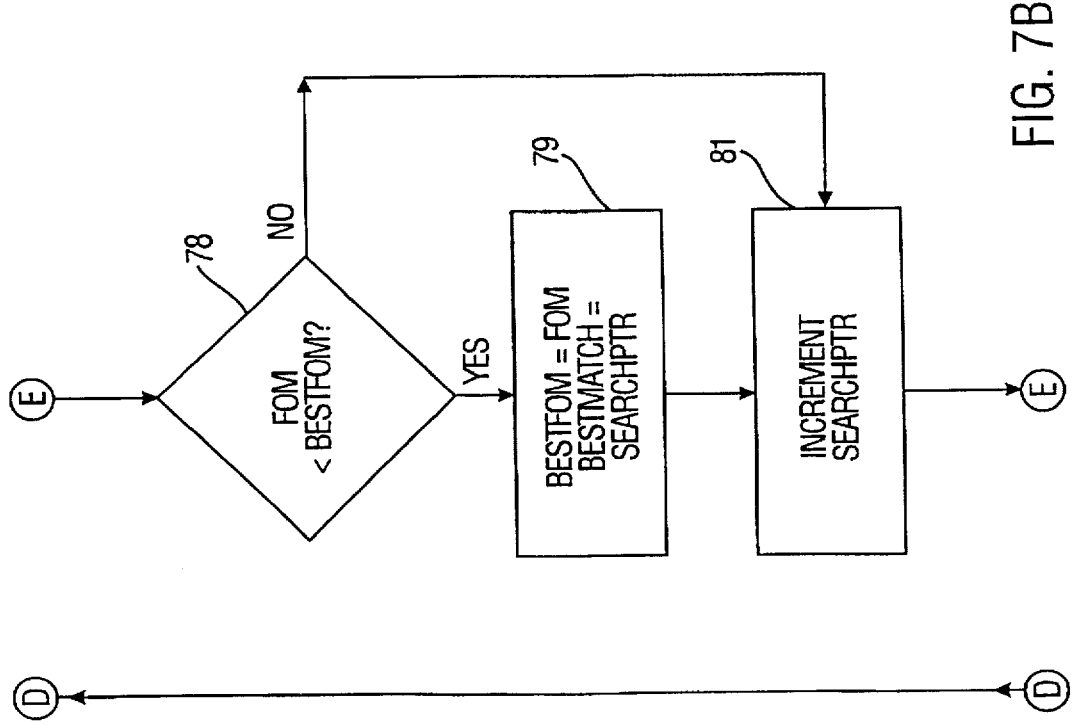
Figure 7C:
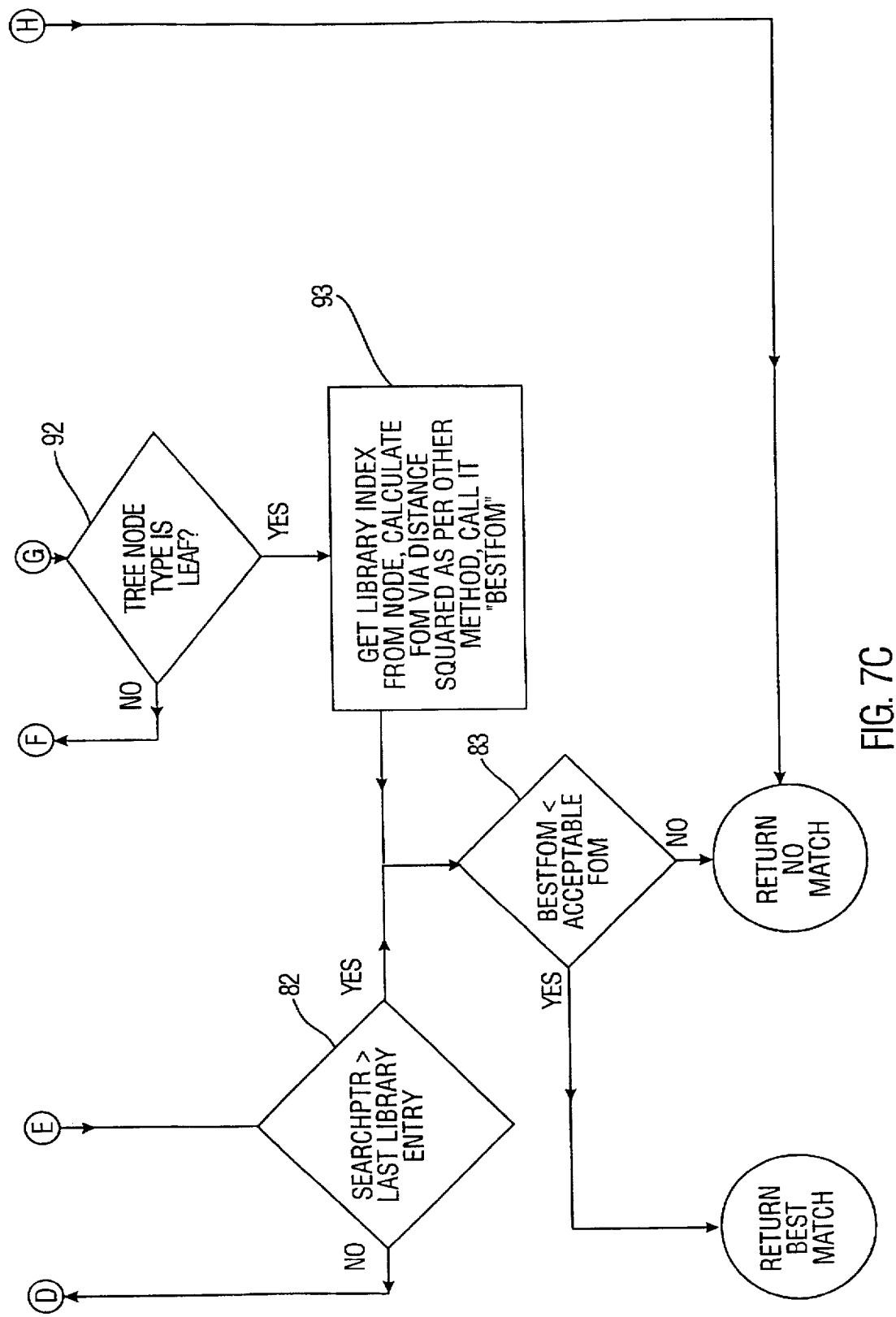

If decision block 66 determines that the total count is above the predetermined threshold, control passes to block 68 where the composition of the glass is determined, in accordance with the method presented in more detail with reference to FIGS. 7A–7C.

Control then passes to block 69 where it is determined whether block 68 has found that the glass under consideration matches the spectrum of a glass of known composition. If it does not, control passes to block 71 where the match counter is cleared, and control returns to block 62.

The match counting is a statistical hedge against making errors. Adding data together then comparing the sum has a different error rate than comparing subsets of data to see if all the comparisons agree. The goal of match counting is to use the least amount of data that gives a reliable answer.

If decision block 69 determines that there is a match, control passes to block 70 where the match counter is incremented. Control then passes to block 72 where it is determined whether the match counter has reached a predetermined number, and if so, the occurrence of the match is concluded, and control is returned to block 57 of FIG. 5. If, on the other hand, decision block 72 determines that the match counter criteria has not been met, control is returned to block 62.

Referring now to FIGS. 7A–7C, the details of the glass composition analysis of step 68 are presented. In accordance with the present invention, the detected x-ray spectrum of scattered and fluorescence radiation from glass of unknown composition, is compared to a library of a plurality of spectra of glasses of known spectral composition. In practice, glasses of known composition are placed on x-ray head 20 (see also FIGS. 2A and 2B), and the spectrum detected by detector 22 is recorded in a library. The same procedure is performed for other glasses of known composition. The individual spectra are stored in the form of normalized spectral intensity peaks at predetermined energy levels corresponding to elements contained within the glasses. Elements in typical CRT glass, most of which exhibit clearly definable x-ray fluorescence peaks at specific energy levels, include: silicon (Si), aluminum (Al), magnesium (Mg), calcium (Ca), strontium (St), barium (Ba), lead (Pb), zirconlure (Zr), zinc (Zn), sodium (Na), potassium (K), titanium (Ti), cerium (Ce), antimony (Sb), arsenic (As), fluorine (F), and iron (Fe).

In accordance with the present invention, intensities of the fluorescence spectra at spectral energy levels corresponding to a selected subset of these possible constituent components of CRT glass are selected for inclusion in the library, and are used for comparison against spectra derived from glasses of unknown composition.

For example, in accordance with one embodiment of the present invention, it has been determined that fluorescence intensities for strontium, barium, lead and zirconium are sufficient to permit accurate and reliable discrimination between five known CRT glass compositions. While intensities at these four energy levels have proven sufficient to discriminate between these five known glass compositions, it should be understood that intensities at more or fewer energy levels may be used, without departing from the scope of the present invention.

Referring now to FIGS. 7A–7C, presented are two methods of comparing the spectrum from the unknown sample of glass, with the stored library of spectra of known glass compositions, to determine which, if any, matches the spectrum from the unknown sample.

In block 73, it is determined which method is desired, the "distance method" or the "tree method". If the distance method is desired, control passes to block 74 where certain parameters used in the method are initialized. Then, in block 76, the first library entry is selected. Each entry in the library includes the type (manufacturer) of glass, the bin into which it should ultimately be sorted, and a list of the normalized x-ray intensities for each of the elements of interest, and possibly the scattered x-ray intensity.

Regardless of which sorting method is used, a figure of merit value is calculated. Should the figure of merit value exceed some predetermined threshold value, the accuracy of the identification is determined to be questionable, and the glass under consideration is tagged as unidentified rather than running the risk of an incorrect identification. By making the threshold (or thresholds) for a match figure of merit lower, then the certainty of the identification is increased; however, more glass will end up being unidentified. On the other hand, by making the threshold for a match figure of merit higher, more glass will be identified and sorted into some bin, rather than going into the unidentified bin (bin x). At the same time, the percentage of glass that is incorrectly identified increases.

The first matching method is termed the "distance" method, and begins with block 74 wherein certain parameters are initialized. Then, in block 76, the first library entry is selected, and control passes to block 77 where a figure of merit for that entry is calculated. The figure of merit is based on the square root of the sum of the squares of the differences of the x-ray intensities for each of the characteristic x-ray intensities stored in a library. In two dimensions, this is simply the distance between the unknown and each of the library samples.

As an example, assume the following library entries exist, each including sample identification followed by four normalized x-ray intensities:

| Sample Name | Intensity 1 | Intensity 2 | Intensity 3 | Intensity 4 |
|---|---|---|---|---|
| A | 0.1 | 0.2 | 0.3 | 0.4 |
| B | 0.2 | 0.2 | 0.3 | 0.3 |
| C | 0.25 | 0.25 | 0.25 | 0.25 | also assume the following spectrum for the unknown:

| Sample Name | Intensity 1 | Intensity 2 | Intensity 3 | Intensity 4 |
|---|---|---|---|---|
| Unknown | 0.22 | 0.18 | 0.31 | 0.29 |

The distance from the unknown sample to each of the library entries is calculated by taking the square root of the sum of the squares of the differences between the unknown's normalized x-ray intensities and each of the standards.

A spreadsheet showing the "figure of merit" for each of the samples follows:

| | Intensity 1 | Intensity 2 | Intensity 3 | Intensity 4 | |
|---|---|---|---|---|---|
| Unknown | 0.22 | 0.18 | 0.31 | 0.29 | |
| | | | | | Figure of Merit |
| A | 0.1 | 0.2 | 0.3 | 0.4 | 0.16 |
| B | 0.2 | 0.2 | 0.3 | 0.3 | 0.03 |
| C | 0.25 | 0.25 | 0.25 | 0.25 | 0.10 |

In this example, library entry B has the smallest figure of merit and is the best match to the unknown sample.

In block 78, the calculated figure of merit is compared against the best existing figure of merit. If the calculated figure of merit is less than the then existing best figure of merit, the present library entry under consideration is determined to be the closest match, so far, to the spectrum of the unknown sample, and control passes to block 79 where the presently calculated figure of merit replaces the best figure of merit, and the present library entry under consideration is stored as the best match (block 79). Control then passes to block 81 where the library pointer index is incremented to the next entry. In decision block 82, it is determined whether all entries in the library have been assessed. If not, control returns to block 77, and if so, control passes to block 83 where the lowest calculated figure of merit is compared to a predetermined threshold to determine whether or not the best calculated figure of merit is sufficiently low to conclude that an accurate match has occurred. If so, the composition of the library entry corresponding most closely to the unknown sample is concluded to be the composition of the unknown sample, and control returns to block 68 of FIG. 6B. If, on the other hand, decision block 83 determines that the best calculated figure of merit is not small enough, it is concluded that no match has occurred, and this information is returned to block 68.

Another search method is termed the "tree" sorting method, and uses the spectral intensities from each of the elements of interest individually, and makes decisions based upon predetermined threshold values. At each step along the tree, the list of possible identification is narrowed. At the end of each branch of the decision tree is a "leaf" that corresponds to a particular library entry that most closes matches the unknown sample.

In particular, beginning in block 84, the tree pointer (TREEPTR) is set to root. Then, in block 86 it is determined whether the tree pointer points to a null, if so, no match is concluded and control is returned to block 68. If, on other hand, the tree pointer is not pointing to a null, control passes to block 87 where the threshold for the node is determined. Then, in block 88, the intensity of the particular element in the unknown sample is compared against the threshold. Depending upon this comparison, branching is accomplished according to steps 89 and 91. Control then passes to block 92 where it is determined whether the thee pointer is on a leaf of a decision tree. If not, control returns to block 86 where the next element intensity from the unknown sample is analyzed, using the threshold from the next node.

If decision block 92 determines that the tree pointer is on a leaf of the decision tree, control passes to block 93 where the particular library entry determined by the decision tree is selected, a figure of merit is calculated using the spectrum selected from the library and the unknown spectrum, using the distance method described above with reference to steps 74 through 82. Then, as before, control passes to block 83 where it is determined whether the calculated figure of merit is small enough so that an accurate match can be concluded. Then control returns to block 68 of FIG. 6B.

Figure 8:
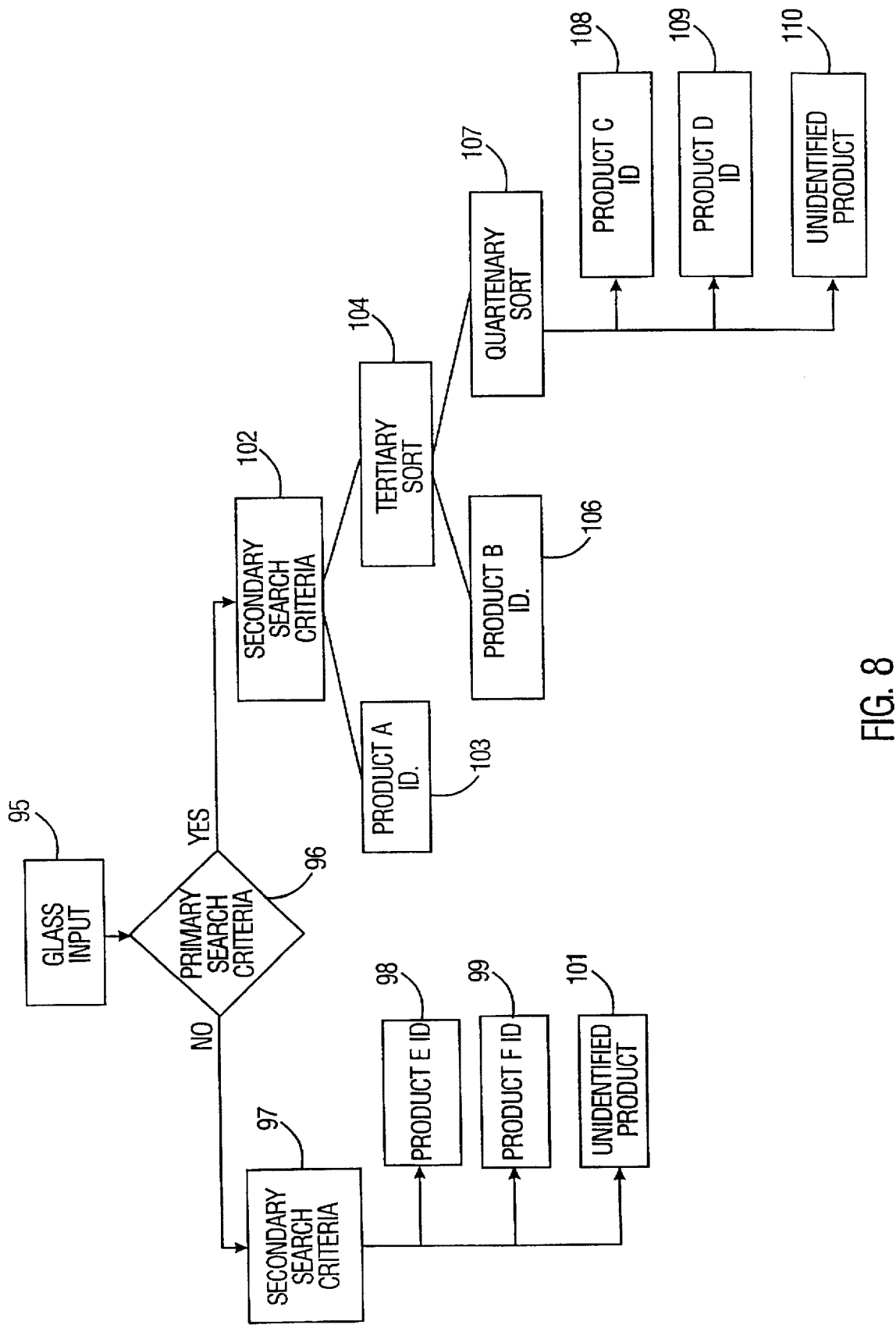
FIGS. 8 is a block diagram of a tree-based library searching method, in accordance with the present invention.

Referring now to FIG. 8, presented is a diagrammatic view of the tree search method presented in flow chart form in steps 84 through 93 of FIGS. 7A–7C. Referring to FIG. 8, an x-ray spectrum for glass of unknown composition (block 95), is applied to the primary search criteria of block 96. This search compares the intensity of a single energy of the fluorescence spectrum (indicative of a single glass component), with a predetermined threshold. For example, if lead exists in the glasses under consideration, the intensity of the unknown spectrum existing at 10.549 keV is compared with a predetermined threshold to determine whether or not lead is present in the glass.

If the primary search criteria in step 96 is not satisfied, control passes to step 97 where secondary search criteria is applied. Similar to the primary search conducted in block 96, the secondary search in block 97 compares the intensity of the fluorescence spectrum of the unknown glass at a particular energy level, which is indicative of a glass component, typically different from the glass component that was the subject of the primary search in block 96. For example, if the primary search is concerned with lead, secondary search 97 may be concerned with strontium.

In the example of FIG. 8, after the secondary search is conducted in block 97, the unknown glass is identifiable as having a composition corresponding to that of either product E or product F. If the figure of merit calculation (performed in step 93 of FIG. 7C), indicates that the figure of merit calculated for the spectrum of unknown intensity is too high, then it is concluded that the composition of the unknown glass cannot be identified (step 101).

If the primary search 96 determines that the intensity of the spectrum at the particular energy level is greater than the predetermined threshold, control passes to block 102 where a secondary search is performed by comparing the intensity of the fluorescence spectrum at an energy level different from the energy level tested in the primary search, block 96, and that intensity is compared against a predetermined threshold.

In the example given, depending on the results of the secondary search conducted in block 102, the unknown glass is concluded to correspond in composition to product A (block 103), or a tertiary search is conducted in block 104.

As with the other searches, the tertiary search conducted in block 104 compares the intensity of the unknown spectrum at a third energy level, indicative of a third glass component, usually different from the glass components under consideration in the primary and secondary searches of steps 96 and 102. If the same element is under consideration, than the threshold is different. For example, a first search could split into low and high lead, then a second search could split the high lead into high and very high lead. The intensity of the unknown glass at that energy level is compared with a threshold, and the results indicate that the unknown glass corresponds to the composition of product B (block 106), or that the quartenary search of block 107 should be conducted.

As with the other search nodes, the quartenary search conducted in block 107 compares the intensity of the spectrum of the glass of unknown composition at a fourth energy level, with a predetermined threshold. In the example illustrated, the results of quartenary search 107 indicate that the glass of unknown composition corresponds to the composition of product C (block 108), correspond to the composition of product D (block 109), or if the calculated figure of merit is too high, that the unknown glass cannot be identified (block 110).

It should be apparent from the description of the tree sorting method described with reference to blocks 84 through 93 of FIGS. 7A–7C and FIG. 8, that the tree may be tuned by adjusting the thresholds used at each node, and by testing for the presence of different glass components (indicated by different energy levels), at each node. In addition, the number of search nodes is variable, and will depend upon the number of possible known glass compositions that are being considered.

Figure 9:
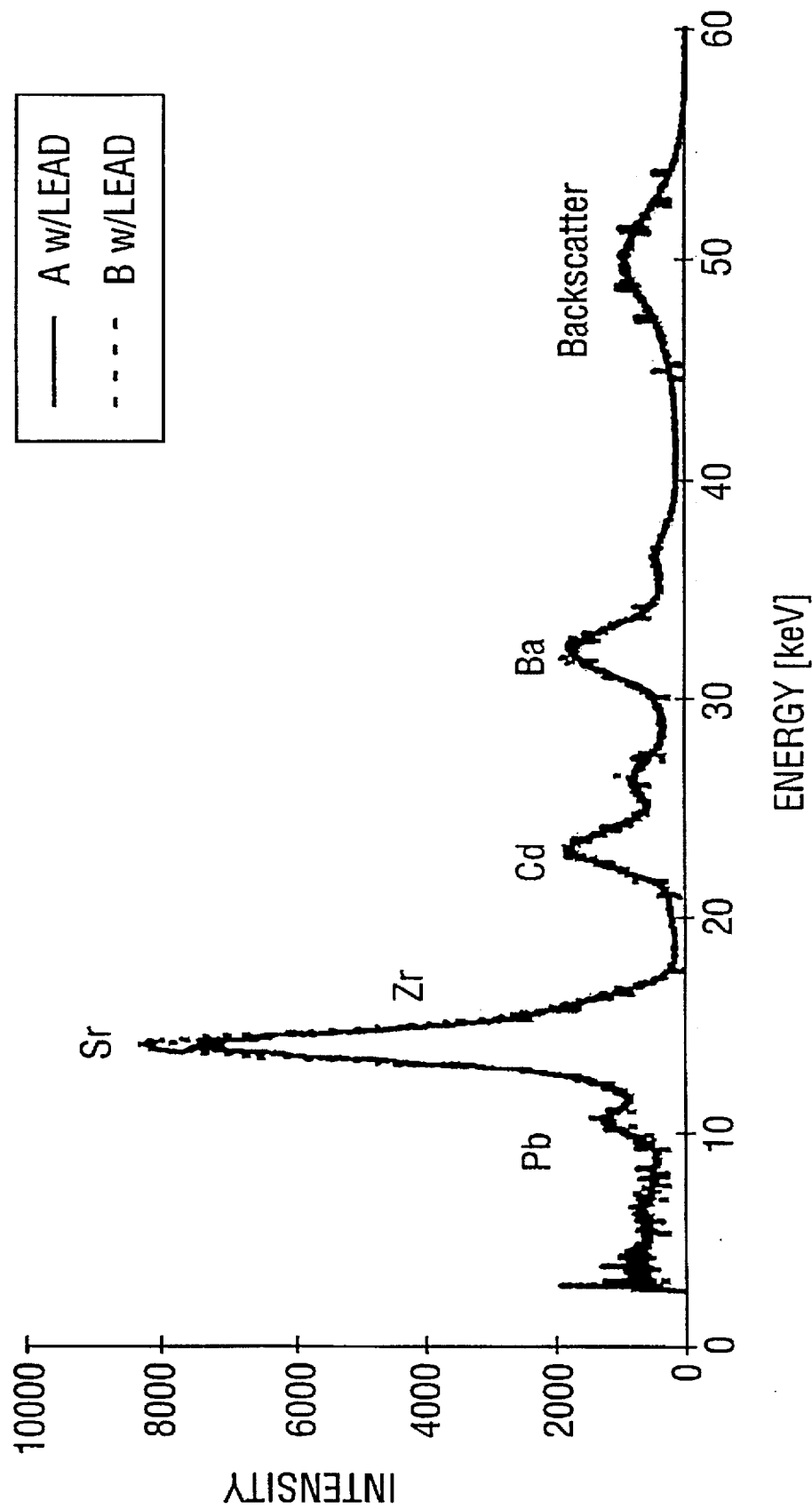
FIGS. 9, 10 and 11 are exemplary x-ray intensity spectra, illustrating various features of the present invention.

Referring now to FIG. 9, presented in graphical form are the fluorescence spectra of two products (product A and product B), superimposed upon one another. As can be seen, the two spectra indicate that the two glasses are nearly identical in composition, with only small differences in the quantity of strontium (14.142 keV) existing between the two samples. The levels of Pb (10.549 keV), Zr (15.746 keV), and Ba (32.066 keV), being virtually identical for the two samples. The cadmium peak (23.109 keV) is due to the cadmium collimator used with the x-ray source 21 (FIGS. 2A and 2B), and is not used in the determination of glass composition. Backscatter is also present at approximately the energy level of the x-ray source.

Figure 10:
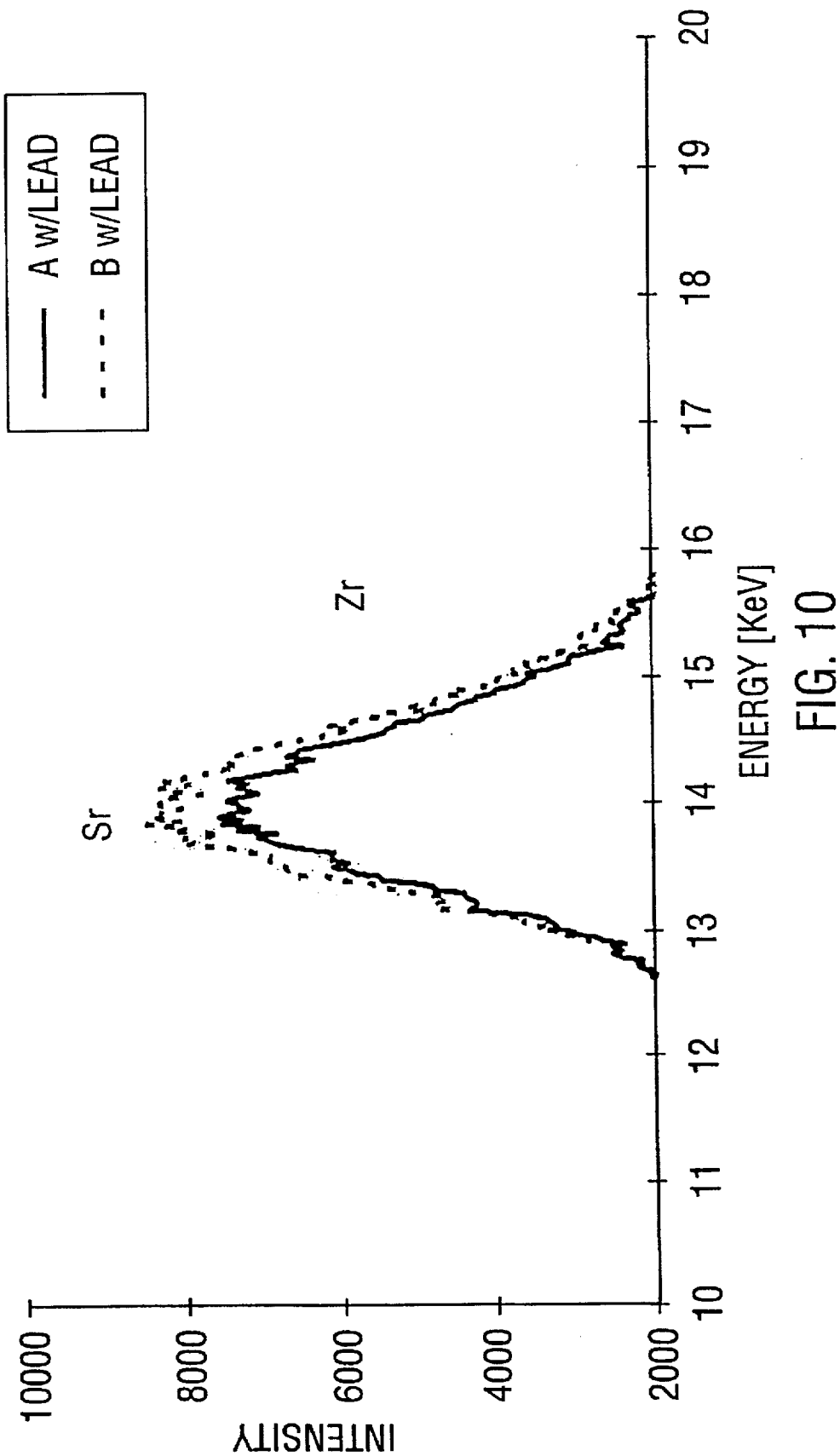

FIG. 10 presents a magnified view of the Sr spectral region of the spectra of FIG. 9, indicating that the two spectra differ in intensity by approximately 1,000 units in this region. In accordance with the present invention, the library entries for products A and B would include the intensity of Sr, and the difference in intensities will permit the correct characterization of glass of unknown composition, as corresponding to either product A or B, using the methods described above.

Figure 11:
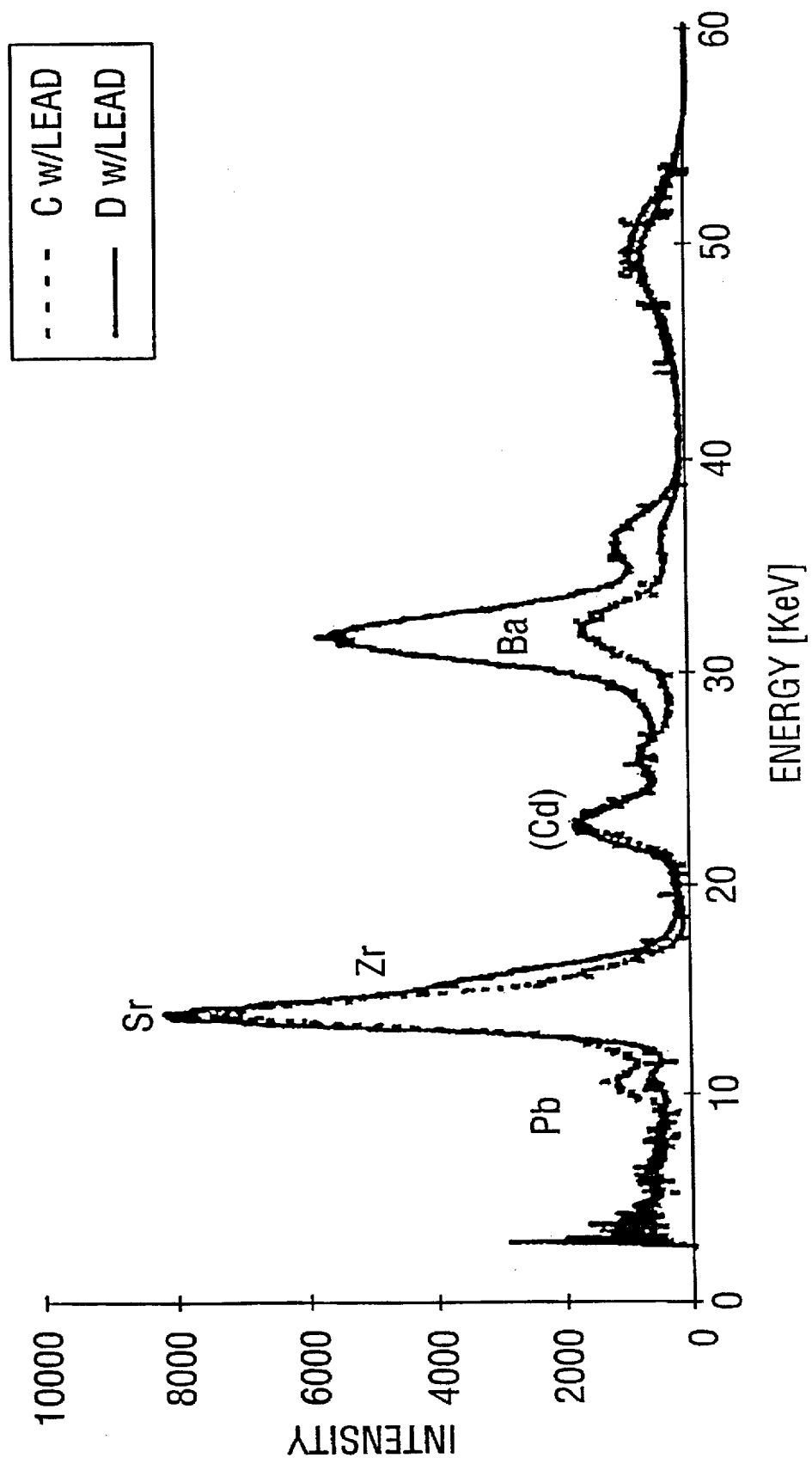

Referring to FIG. 11, presented are two additional fluorescence spectra for products C and D of known composition. As can be seen, these two products correspond in the quantity of Sr, but differ greatly in the quantities of Pb and Ba. The large difference in the Ba content between products C and D indicate that Ba (32.066 keV), would be a useful energy level of the fluorescence spectrum to discriminate between products C and D for one of the nodes of the tree search method illustrated in steps 84 through 93 of FIGS. 7A–7C and illustrated in FIG. 8.

It will be understood that although the present invention has been described with reference to particular embodiments, additions, deletions and changes could be made to these embodiments, without departing from the scope of the present invention.

What is claimed is:

1. A method of identifying a composition of at least one glass piece of a substantially continuous series of glass pieces of unknown composition, comprising:

irradiating said glass piece of unknown composition with x-rays;

detecting an x-ray fluorescence spectrum emanating from said glass piece of unknown composition;

automatically comparing said detected spectrum with at least one of a plurality of stored predetermined x-ray fluorescence spectra, each stored spectra corresponding to glass of known composition; and identifying a composition of said glass piece of unknown composition as a function of said comparison.

2. The method of claim 1, said irradiating step comprising:

conveying said glass piece while irradiating said glass piece.

3. The method of claim 1, said detecting step comprising:

conveying said glass piece while detecting said x-ray fluorescence spectrum emanating from said glass piece.

4. The method of claim 1, further comprising:

normalizing said detected spectra to adjust for varying geometry of said series of glass pieces.

5. The method of claim 4, said normalizing step comprising:

dividing intensities of said detected spectrum occurring at each of a plurality of selected energy levels within said spectrum, by a sum of said intensities, to produce a normalized intensity at each of said plurality of energy levels.

6. The method of claim 5, further comprising:

selecting said plurality of energy levels to correspond to fluorescence peaks of elemental components of glass.

7. The method of claim 1, said detecting step comprising:

determining the presence or absence of a piece of glass as a function of said detected spectrum.

8. The method of claim 1, further comprising:

a. a radiating glass of known composition;
b. detecting a fluorescence spectrum from said glass of known composition;
c. determining a plurality of intensities of said fluorescence spectrum at energy levels corresponding to predetermined glass components;
d. storing said plurality of intensities as one of said plurality of predetermined x-ray fluorescence spectra; and repeating each of steps a–d for other glass of known composition.

9. The method of claim 8, said comparing step comprising:

automatically comparing intensities of said detected spectrum of said glass of unknown composition at said energy levels corresponding to said predetermined glass components, with respective intensities in each of said predetermined x-ray fluorescence spectra.

10. The method of claim 9, said step of determining composition of said glass of unknown composition comprising:

calculating a figure of merit for each of said plurality of predetermined x-ray fluorescence spectra by calculating the square root of the sum of the squares of the differences of the intensities of said detected spectrum of glass of unknown composition and the respective intensities in said predetermined x-ray fluorescence spectra; and determining that said glass of unknown composition corresponds to the composition of the glass with the predetermined x-ray fluorescence spectrum having a minimum figure of merit.

11. The method of claim 1, further comprising:

sorting said glass of unknown composition according to determined composition.

12. A glass cullet processing apparatus, comprising:

an x-ray source and an x-ray fluorescence detector, each located adjacent a glass testing position;

means for conveying glass cullet to and from said glass testing position; and data processing means, connected to said detector and including a stored library of x-ray fluorescence spectra of glass of known composition, for comparing an x-ray fluorescence spectrum obtained from glass cullet in said glass testing position with each spectra in said library, and for providing an indication of glass cullet identification as a function of the comparison.

13. The apparatus of claim 12, further comprising:

means, responsive to said indication of glass cullet composition, for diverting said glass cullet from said means for conveying into one of a plurality of containers.

14. A method of identifying a composition of at least one glass piece of a substantially continuous series of glass pieces of unknown composition, comprising:

irradiating said at least one glass piece of unknown composition with x-rays;

detecting an x-ray fluorescence spectrum emanating from said at least one glass piece of unknown composition;

determining intensities of said detected spectrum at predetermined energy levels;

automatically comparing said detected spectrum with at least one of a plurality of stored predetermined x-ray fluorescence spectra, each stored spectrum having predetermined intensities corresponding to glass of known composition, said automatically comparing step comprising, subjecting said predetermined intensities of said stored spectra to a tree-sorting method; and identifying a composition of said at least one glass piece of unknown composition as a function of said comparison.

15. A method of identifying a composition of at least one glass piece of a substantially continuous series of glass pieces of unknown composition, comprising:

irradiating said at least one glass piece of unknown composition with x-rays;

detecting an x-ray fluorescence spectrum emanating from said at least one glass piece of unknown composition;

determining intensities of said detected spectrum at predetermined energy levels;

automatically comparing said detected spectrum with at least one of the plurality of stored predetermined x-ray fluorescence spectra, each stored spectra corresponding to glass of known composition, by calculating a figure of merit for each of said plurality of predetermined x-ray fluorescence spectra relative to said detected spectrum; and identifying a composition of said at least one glass piece of unknown composition to correspond to a composition of glass of known composition with a predetermined x-ray fluorescence spectrum having a minimum figure of merit.

16. The method of claims 15, said calculating step comprising:

calculating said figure of merit for each of said plurality of stored predetermined x-ray fluorescence spectra by calculating a square root of a sum of the squares of the differences of the intensities of said detected spectrum of glass of unknown composition and the respective intensities in said predetermined x-ray fluorescence spectra.

* * * * *

UNITED STATES PATENT AND TRADEMARK OFFICE
CERTIFICATE OF CORRECTION

PATENT NO. : 5,663,997

DATED : September 2, 1997

INVENTOR(S) : James E. Willis, Andrew L. Heilveil and Robert Dejaiffe

It is certified that error appears in the above-identified patent and that said Letters Patent is hereby corrected as shown below:

In claim 12, column 12, line 3, delete "each" and insert --at least one-- therefor.

Signed and Sealed this

Second Day of December, 1997

Attest:

Attesting Officer

BRUCE LEHMAN

Commissioner of Patents and Trademarks